| United States Patent [19] | [11] Patent Number: 4,521,409 |
| Bauman | [45] Date of Patent: Jun. 4, 1985 |

[54] USE OF GROWTH HORMONE TO ENHANCE RUMINANT MAMMARY DEVELOPMENT

[75] Inventors: Dale E. Bauman, Ithaca, N.Y.; Kris Sejrsen, Havndal, Denmark

[73] Assignee: Cornell Research Foundation, Inc., Ithaca, N.Y.

[21] Appl. No.: 538,638

[22] Filed: Oct. 3, 1983

[51] Int. Cl.$^3$ ..................... A61K 37/00; A61K 35/55
[52] U.S. Cl. .................................... 514/21; 424/108; 514/2
[58] Field of Search ................................ 424/177, 108

[56] References Cited

PUBLICATIONS

"Hyprophyseal Growth Hormone, Nature and Actions", 1955, R. W. Smith, ed., McGraw Hill, N.Y., pp. 486-492.
Chung, J. Dairy Science, 38:609, (1955).
Brumby et al., N.Z.J. Science & Technology, A38:1-52-156, (1956).
Mellenberger et al., Biochem. J., 136:741-748, (1973).
Collier et al., Endocrinology, 100:1192-1200 (1977).
Akers et al., Endocrinology, 109:23-40, (1981).
Sejrsen, Acta Agric. Scandinavica, 1978, 28:41-45.
Sejrsen et al., Livestock Prod. Sci., 1977, 4:313-325.
Sejrsen et al., J. Dairy Sci., 1982, 65:763-800.
Tucker, J. Dairy Sci., 1981, 64:1403-1421.
Bauman et al., 1982, J. Dairy Sci., 65:(Suppl. 1):188.
Peel et al., J. Nutrition, 1981, III: 1662-1671.
Forsyth et al., "Biochemistry of Lactation" (Mepham. Ed.), Elsevier Science Publishers, 1983, pp. 309-349.
Bines et al., J. Dairy Sci., 1982, 65: 1375-1389.
Hart-Chem. Abst. vol. 93, (1980), p. 89,185e.
Marchenko et al., Chem. Abst. vol. 91, (1979), p. 14,326b.

*Primary Examiner*—Sam Rosen

[57] ABSTRACT

This invention relates to the administration of growth hormone to a ruminant between about the onset of puberty to about first parturition, thereby increasing the quantity of mammary parenchyma, resulting in increased milk production during subsequent lactations.

6 Claims, 2 Drawing Figures

HEIFER MAMMARY GLAND
PLACEBO

HEIFER MAMMARY GLAND
GROWTH HORMONE

USE OF GROWTH HORMONE TO ENHANCE RUMINANT MAMMARY DEVELOPMENT

BACKGROUND OF THE INVENTION

The effect of growth hormone on maturing or mature ruminants has been examined from time to time, but to date the administration of growth hormone within a finite period has not been recognized as useful in obtaining a permanent increase in milk production in a ruminant.

Peel et al, *J. Nutrition*, 1981, 111:1662–1671, describes the administration of bovine growth hormone to high yield cows and demonstrates that at peak milk production the administration growth hormone enhances milk production. Milk production returned to normal levels following cessation of the treatment.

Bauman et al, 1982, *J. Diary Sci.* 65 (Suppl.1):188, reported that recombinantly derived bovine growth hormone enhanced milk production and improved feed efficiency in a manner similar to the biological responses observed with natural bovine growth hormone.

Tucker, *J. Dairy Sci.*, 1981, 64:1403–1421 inter alia discusses factors which affect mammary growth, including apparent interaction of estradiol-17$\beta$, progesterone, prolactin, growth hormone and placental lactogen to synergize to stimulate mammary growth.

Sejrsen, *Acta Agric. Scandinavica*, 1978, 28:41–45, discusses the fact that a major part of the development of the mammary glands takes place between birth and 1st calving and apparently is affected, in part, by growth hormone levels.

Bauman et al, 1979, *J. Dairy Sci.* 62 (Suppl. 1):114, describe the effect of energy intake upon serum concentrations of prolactin and growth hormone in lactating cows.

Sejrsen et al, *Livestock Prod. Sci.*, 1977, 4:313–325, and *J. Dairy Sci.*, 1982, 65:793–800 discuss the effect of nutrition on growth rate, mammary development and milk yield.

DESCRIPTION OF THE INVENTION

Figure 1:
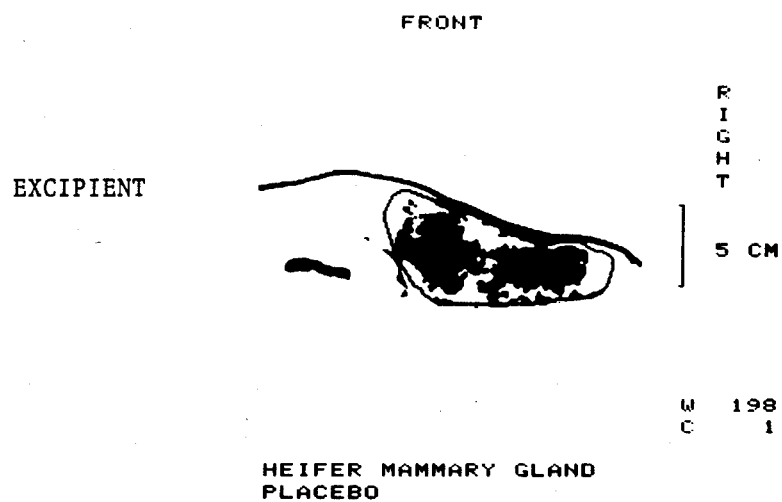
FIG. 1 is a cross section area of the mammary gland of the excipient treated heifer of pair 2.

This invention relates to the administration of growth hormone to a ruminant between about the onset of puberty to about first parturition and preferably between about the onset of puberty to about first conception, thereby increasing the quantity of mammary parenchyma, resulting in increased milk production during subsequent lactations.

This invention is particularly useful when applied to ruminants which are economically significant commercial milk sources, for example cows, especially dairy cows and also sheep and goats, although the benefit of increased milk production is also significant where the animal's milk is primarily only for the nourishment of its young.

As is known in the art, growth hormones among ruminants are related materials which display heterotypic activity. Thus, the growth hormone administered to the ruminant need not be the same hormone naturally occurring in the particular ruminant, but can be any ruminant growth hormone which displays growth hormone activity in the ruminant being treated. Preferably, the growth hormone employed for a particular ruminant is the same growth hormone which is found naturally occurring in the ruminant being treated.

The growth hormone can be a naturally occurring growth hormone, for example isolated from animal tissues or a body fluid (for example bovine growth hormone isolated from pituitary glands), or can be a synthetic equivalent of a naturally occurring growth hormone, for example a growth hormone produced by recombinant DNA techniques. As noted above, recombinantly derived bovine growth hormone is known to the art.

The growth hormone is administered to the ruminant in a parenchyma tissue enhancing amount for a time sufficient to provide increased parenchyma tissue production. Typically the amount of growth hormone administered is in the range of about 0.05 to about 0.2 milligrams per kilogram of ruminant body weight, daily. An effective amount can be monitored by increased serum growth hormone levels as compared to the animal when the exogenous hormone is withdrawn.

The period during which administration of growth hormone is conducted to achieve increased mammary parenchyma and thus an increase in milk production during subsequent lactations appears to be reasonably critical. For the purposes of this invention growth hormone must be administered between about the onset of puberty and about first parturition, and preferably between about the onset of puberty and about first conception, in order to achieve increased mammary parenchyma. Most preferably the growth hormone is administered substantially throughout the above described interval. However, shorter administration intervals which still produce increased mammary parenchyma are contemplated as useful. Usually the time between the onset of puberty and first conception is in the order of 100 days. Time periods of at least about 25 days and preferably at least about 50 days would appear to provide useful results.

The growth hormone can be administered in any manner adapted to cause entry of the growth hormone into the ruminant blood stream. For example, while subcutaneous injection is presently preferred, the growth hormone can also be given intramuscularly or intravenously. The use of time release implants is also contemplated.

EXAMPLE

Pairs of identical twins (dairy heifers) were randomly assigned to receive either exogenous bovine growth hormone or excipient treatments. Daily subcutaneous injections of growth hormone (20 mg/day) or excipient commenced shortly before heifers reached puberty (approximately 200 kg body weight) and continued for approximately 100 days. On the last treatment day, heifers were killed and the mammary glands excised. The total quantity of mammary parenchyma was quantified by 3-dimensional, computerized, X-ray tomography.

Results

| Pair Number | Treatment | | Percent Increase with Growth Hormone |
| --- | --- | --- | --- |
| | Excipient | Growth Hormone | |
| 1 | 115.05 | 124.72 | +8.4% |
| 2 | 189.18 | 237.28 | 25.4% |
| mean | 152.18 | 181.00 | — |
| relative | 100 | 119 | +19% |

Figure 2:
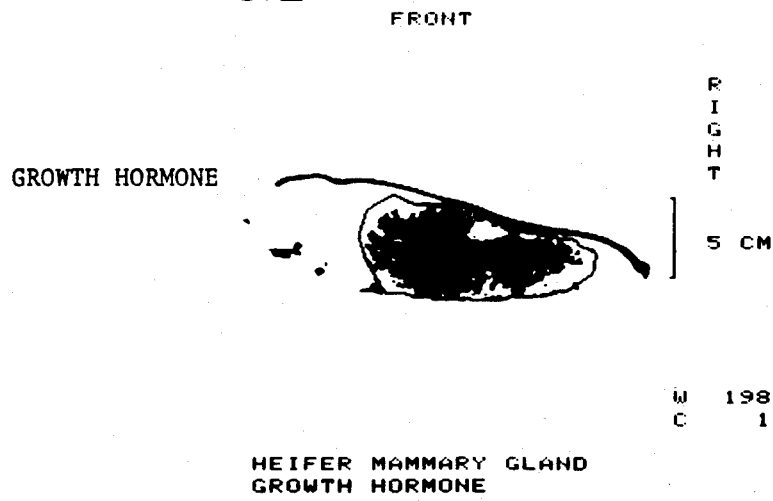
FIG. 2 is a cross section area of the mammary gland of the growth hormone treated heifer of pair 2 as determined by X-ray tomography. The micrographs show parenchyma tissue as dark area and fat tissue as white area within the mammary gland (generally oval shaped outline).

FIG. 1 is a cross section area of the mammary gland of the excipient treated heifer of pair 2, and FIG. 2 is a cross section area of the mammary gland of the growth hormone treated heifer of pair 2 as determined by X-ray tomography. The micrographs show parenchyma tissue as dark area and fat tissue as white area within the mammary gland (generally oval shaped outline).

I claim:

1. A method of increasing the quantity of mammary parenchyma in a ruminant which comprises administering a mammary parenchyma growth stimulating amount of a ruminant growth hormone to said ruminant between about the onset of puberty and about the first parturition, thereby increasing milk production during subsequent lactations.

2. A method as in claim 1 where the growth hormone is administered between about the onset of puberty and first conception.

3. The method of claim 1 where the ruminant is a cow.

4. The method of claim 1 where the growth hormone is exogenous hormone equivalent to the hormone naturally produced by the ruminant.

5. The method of claim 4 where the growth hormone is isolated from pituitary gland.

6. The method of claim 4 where the rumnant is a cow and the growth hormone is recombinantly derived bovine growth hormone.

* * * * *